United States Patent [19]

Reap

[11] 4,394,153

[45] Jul. 19, 1983

[54] HERBICIDAL ARYL ESTERS OF N-[(HETEROCYCLIC)-AMINOCARBONYL]-SULFAMIC ACID

[75] Inventor: James J. Reap, Wilmington, Del.

[73] Assignee: E. I. Du Pont de Nemours and Company, Wilmington, Del.

[21] Appl. No.: 261,751

[22] Filed: May 18, 1981

Related U.S. Application Data

[63] Continuation-in-part of Ser. No. 168,345, Jul. 11, 1980, abandoned.

[51] Int. Cl.$^3$ .................. A01N 9/22; C07D 239/32
[52] U.S. Cl. .................................. 71/92; 71/93; 544/208; 544/211; 544/253; 544/278; 544/317; 544/321; 544/323; 544/332
[58] Field of Search .................. 544/321, 323, 332; 71/92

[56] References Cited

U.S. PATENT DOCUMENTS

| | | | |
|---|---|---|---|
| 4,169,719 | 10/1979 | Levitt | 544/332 |
| 4,190,432 | 2/1980 | Levitt | 544/323 |
| 4,231,784 | 11/1980 | Levitt | 71/92 |
| 4,302,241 | 11/1981 | Levitt | 544/332 |
| 4,310,346 | 1/1982 | Levitt | 544/323 |

Primary Examiner—Donald G. Daus
Assistant Examiner—James H. Turnipseed

[57] ABSTRACT

The compounds are of the class of aryl esters of N-[(heterocyclic)aminocarbonyl]sulfamic acid, such as N-[(4,6-dimethoxypyrimidin-2-yl)aminocarbonyl]sulfamic acid, (2-methylsulfonyloxy)-phenyl ester, useful for weed control in crops, brush control and plant growth retardation.

28 Claims, No Drawings

HERBICIDAL ARYL ESTERS OF N-[(HETEROCYCLIC)-AMINOCARBONYL]SULFAMIC ACID

RELATED APPLICATION

This application is a continuation-in-part of my copending application U.S. Ser. No. 168,345, filed July 11, 1980 (now abandoned).

BACKGROUND OF THE INVENTION

This invention relates to aryl N-(heterocycliccarbamoyl)arylsulfamates and their use as agricultural chemicals.

Chem. Ber., 105, 2791 (1972) describes the preparation of N-butylcarbamoyl-p-toluenesulfamate, but does not claim utility as a pesticide:

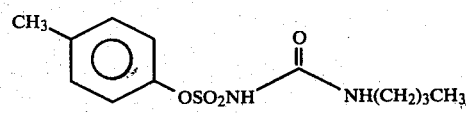

German Pat. No. 940,292 describes the preparation of N-[arylcarbamoyl]arylsulfamides and claims utility as textile assistants, pharmaceuticals and pesticides:

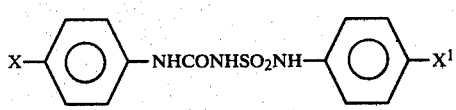

wherein each of X and $X^1$ is H, or each is ethoxy.

Netherlands Pat. No. 121,788, published Sept. 15, 1966, teaches the preparation of the following compounds and their use as general or selective herbicides:

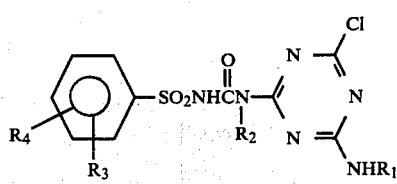

wherein
  $R_1$ and $R_2$ may independently be alkyl of 1-4 carbon atoms; and
  $R_3$ and $R_4$ may independently be hydrogen, chlorine or alkyl of 1-4 carbon atoms.

French Pat. No. 1,468,747 discloses para-substituted phenylsulfonamides, useful as antidiabetic agents:

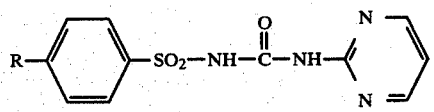

wherein
  R=H, halogen, $CF_3$ or alkyl.

Logemann et al. Chem. Ab., 53, 18052 g (1959), disclose a number of sulfonamides, including uracil derivatives and those having the formula:

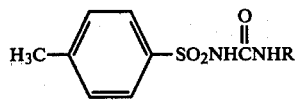

wherein
  R is butyl, phenyl or

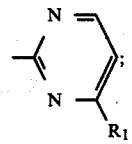

and
  $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

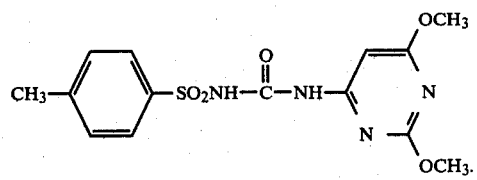

Based upon similarity to a known compound, the author predicted hypoglycemic activity for the foregoing compound.

U.S. Pat. No. 4,191,553 to James Reap teaches agricultural compounds of the general formula:

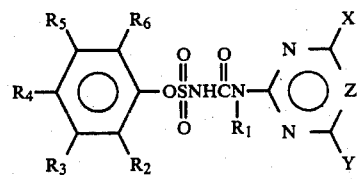

wherein
  $R_1$ is H, $OCH_3$ or alkyl of 1-3 carbons;
  $R_2$ is H, Cl, F, Br, $NO_2$, alkyl of 1-4 carbons, alkoxy of 1-4 carbons, $CF_3$ or

$R_3$ is H, Cl, F, Br, $CH_3$ or alkoxy of 1-4 carbons;
  $R_4$ is H, Cl, F, Br, $NO_2$, alkyl of 1-4 carbons, alkoxy of 1-4 carbons, CN or

$R_5$ is H, Cl, F, Br, $CH_3$, $NO_2$ or $CF_3$;

$R_6$ is H, Cl, F, Br, alkyl of 1-4 carbons or alkoxy of 1-4 carbons;

$R_7$ is $-ONA^\oplus$, OH or alkoxy of 1-4 carbons;

X is $CH_3$, $CH_3CH_2$, alkoxy of 1-3 carbons, $CH_3OCH_2$, $CH_3OCH_2CH_2O$, $CH_3S$, $CH_3CH_2S$, $CF_3$ or Cl;

Y is $CH_3$, $CH_3CH_2$, alkoxy of 1-3 carbons, $CH_3OCH_2$, $CH_3OCH_2CH_2O$, $CH_3S$ or $CH_3CH_2S$; and Z is CH or N; provided that -only one of $R_2$, $R_3$ or $R_4$ is alkoxy; and -when $R_5$ is $NO_2$, $R_4$ is other than $NO_2$.

Undesired vegetation can cause substantial damage to useful crops, especially agricultural products that satisfy man's basic food and fiber needs, such as cotton, rice, corn, wheat, soybean and the like.

Although a wide variety of materials are available which can be used for killing or inhibiting (controlling) the growth of undesired vegetation the need exists for still more effective herbicides that destroy or control weeds without causing significant damage to useful crops.

SUMMARY OF THE INVENTION

This invention relates to novel compounds of Formula I, to compositions containing them and to their method of use as general as well as selective pre- and post-emergence herbicides.

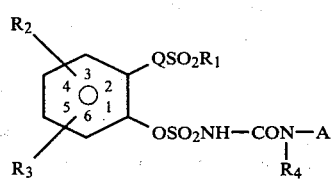

I where

Q is O or $NR_5$;

$R_1$ is $C_1-C_4$ alkyl, $C_1-C_4$ alkyl substituted with 1-3 atoms of F, Cl or Br, $CH_2CH_2OCH_3$, $CH_2CH_2CH_2OCH_3$ or

;

$R_2$ is H, F, Cl, Br, $OCH_3$, $NO_2$ or $C_1-C_2$ alkyl;

$R_3$ is H, F, Cl, Br or $CH_3$;

$R_4$ is H, $CH_3$ or $OCH_3$;

$R_5$ is $C_1-C_4$ alkyl;

$R_6$ and $R_7$ are independently H, F, Cl, Br, $CH_3$, $CF_3$, $NO_2$ or $OCH_3$;

A is

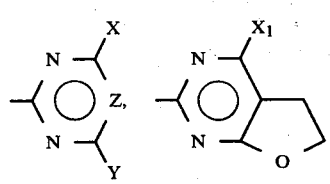

-continued

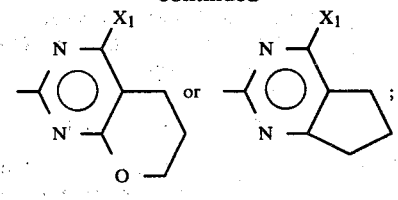

X is $NH_2$, $N(CH_3)_2$, $NHCH_3$, $C_1-C_4$ alkyl, $CH_2OCH_3$, $CH_2OC_2H_5$, $C_1-C_3$ alkoxy, $C_3-C_4$ alkenyloxy, $C_3-C_4$ alkynyloxy, $OCH_2CF_3$ or $C_1-C_3$ alkyl substituted with 1-3 atoms of F, Cl or Br;

Y is H, $CH_3$, $OCH_3$ or Cl;

$X_1$ is H, $CH_3$, $OCH_3$ or Cl; and

Z is CH, N, $CCH_3$, CBr, CCl, CF or CI;

provided that:

(1) when Y is Cl, then Z is CH and X is $NH_2$, $NHCH_3$, $N(CH_3)_2$, $CH_3$ or $OCH_3$; and (2) when Y is H, then X is $OCH_3$, $CH_3$ or $CH_2OCH_3$, and Z is CH, $CCH_3$, CBr, CCl, CF or CI.

Preferred for reasons of higher herbicidal activity and/or more favorable ease of synthesis are:

(1) Compounds of the generic scope where $R_5$ is $CH_3$ and $R_4$ is H or $CH_3$;

(2) Compounds of preferred (1) where $R_1$ is $C_1-C_4$ alkyl or $CF_3$;

(3) Compounds of preferred (2) where $R_2$ is H;

(4) Compounds of preferred (3) where $R_3$ is H;

(5) Compounds of preferred (4) where $R_1$ is $C_1-C_3$ alkyl or $CF_3$;

Q is O;

A is

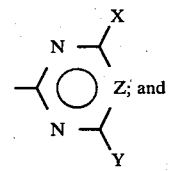

Z is CH or N;

(6) Compounds of preferred (5) where $R_4$ is H; and (7) Compounds of preferred (6) where X and Y are independently $CH_3$ or $OCH_3$, and $R_1$ is $CH_3$.

Specifically preferred for highest herbicidal activity and/or most favorable ease of synthesis are:

N-[(4,6-dimethoxypyrimidin-2-yl)aminocarbonyl]sulfamic acid, [2-(methylsulfonyloxy)phenyl]ester;

N-[(4-methoxy-6-methylpyrimidin-2-yl)aminocarbonyl]-sulfamic acid, [2-(methylsulfonyloxy)phenyl]-ester;

N-[(4,6-dimethylpyrimidin-2-yl)aminocarbonyl]sulfamic acid, [2-(methylsulfonyloxy)phenyl]ester;

N-[(4,6-dimethoxy-1,3,5-triazin-2-yl)aminocarbonyl]-sulfamic acid, [2-(methylsulfonyloxy)phenyl]ester;

N-[(4,6-dimethyl-1,3,5-triazin-2-yl)aminocarbonyl]-sulfamic acid, [2-(methylsulfonyloxy)phenyl]ester; and N-[(4-methoxy-6-methyl-1,3,5-triazin-2-yl)aminocarbonyl]sulfamic acid, [2-(methylsulfonyloxy)phenyl]ester.

This invention also relates to compounds of Formula IV which are useful intermediates for the preparation of the herbicidal compounds of Formula I:

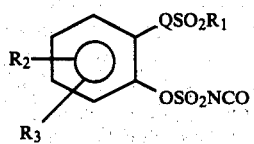

where
Q is O or $NR_5$;
$R_1$ is $C_1$–$C_4$ alkyl, $C_1$–$C_4$ alkyl substituted with 1–3 atoms of F, Cl or Br, $CH_2CH_2OCH_3$, $CH_2CH_2CH_2OCH_3$ or

$R_2$ is H, F, Cl, Br, $OCH_3$, $NO_2$ or $C_1$–$C_4$ alkyl;
$R_3$ is H, F, Cl, Br or $CH_3$;
$R_5$ is $C_1$–$C_4$ alkyl; and
$R_6$ and $R_7$ are independently H, F, Cl, Br, $CH_3$, $CF_3$, $NO_2$ or $OCH_3$.

Preferred intermediates, for reasons of more favorable ease of synthesis and/or higher herbicidal activity of the compounds of Formula I, are:

(1) Compounds of Formula IV where Q is O, $R_2$ and $R_3$ are H, and $R_1$ is $CH_3$ or $CF_3$; and
(2) Compounds of Formula IV where Q is $NCH_3$, $R_2$ and $R_3$ are H, and $R_1$ is $CH_3$ or $CF_3$.

Synthesis

The compounds of this invention can be made as outlined in Schemes 1, 2, 3 and 4 below. The compounds of Formula (V), (VI) or (X) can be prepared by reacting an appropriate 2-aminopyrimidine, 2-aminotriazine or 2-aminobicyclopyrimidine of Formula (II), (III) or (IX) with an appropriately substituted aryloxysulfonyl isocyanate of Formula (IV).

Scheme 1

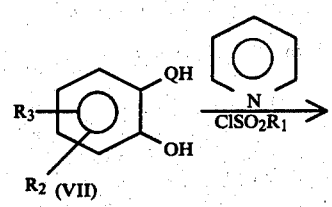

Scheme 2

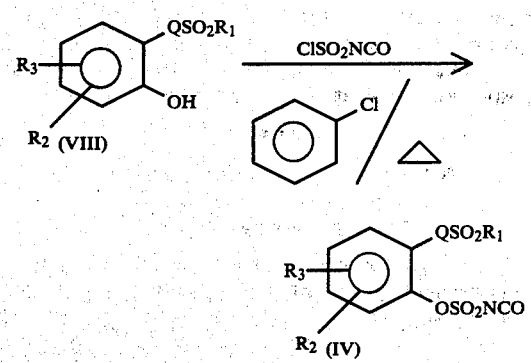

Scheme 2

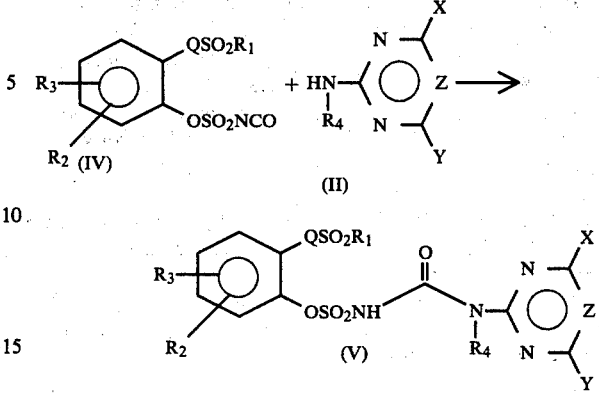

Scheme 3

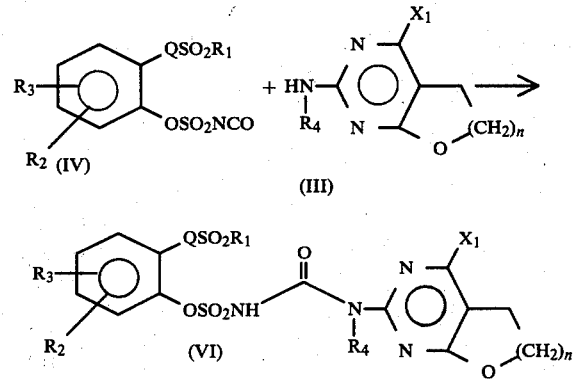

Scheme 4

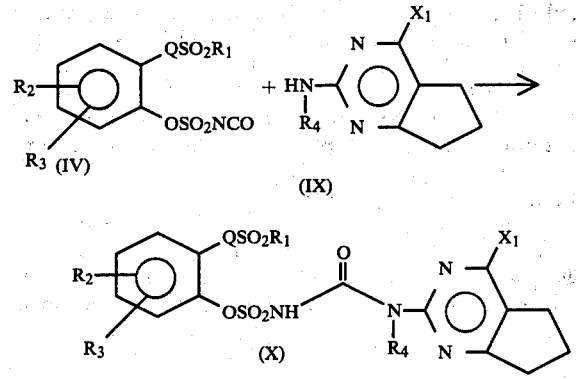

where
Q, $R_1$, $R_2$, $R_3$, $R_4$, X, Y, Z, and $X_1$ are as previously defined above, and n is 1 or 2.

The reaction is best carried out in inert solvents such as methylene chloride and acetonitrile. The mode of addition is not critical, however, it is often convenient to add a solution of the isocyanate (IV) to a stirred suspension of the amino heterocycle (II), (III) or (IX).

The reaction is generally exothermic. In some cases, the desired product is insoluble in the reaction medium and crystallizes from it in pure form. Products soluble in the reaction medium are isolated by evaporation of the solvent and trituration of the residue with solvents such as ethyl ether, 1-chlorobutane or hexanes and filtration.

The intermediate isocyanates of Formula (IV) can be prepared by reacting a substituted phenol of Formula (VIII) with chlorosulfonyl isocyanate and heating to reflux in solvents such as chlorobenzene or xylene according to the procedure of Lohaus, Chem. Ber. 105, 2791 (1972). Chlorosulfonyl isocyanate is commercially available and compounds of Formula (VIII) can be prepared according to the procedure of Kampouris, J. Chem. Soc., 2651 (1965) or German Patent 2,611,599.

The synthesis of the heterocyclicamine derivatives has been reviewed in "The Chemistry of Heterocyclic Compounds", a series published by Interscience Publ., New York and London.

2-Aminopyrimidines are described by D. J. Brown in "The Pyrimidines", Vol. XVI of the above series which are herein incorporated by reference.

The aminoheterocyclic intermediates (II) in which $R_4$ is $CH_3$, may be prepared by the following procedure, or by obvious modifications thereof.

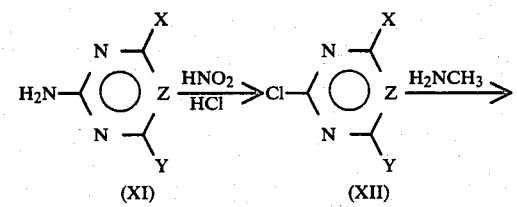

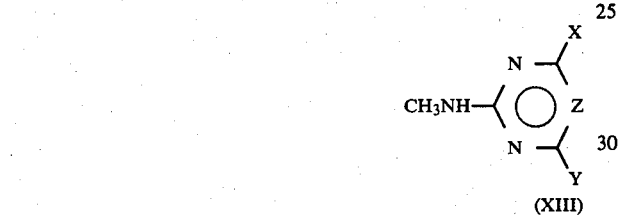

A solution of the amine (XI) in concentrated hydrochloric acid is contacted with an aqueous sodium nitrite solution and the chloro compound (XII) is isolated by filtration of the acidic solution (see for example, Bee and Rose, J. Chem. Soc. C., 2051 (1966) for the case in which Z is CH and X and Y are $OCH_3$). Displacement of the chlorine may be accomplished by heating with an excess of methylamine in water to obtain the methylaminoheterocycle (XIII).

N-Methoxyamino heterocycles can be prepared by procedures reported on the literature [see, for example, Belgian Pat. No. 618,563 and J. T. Shaw, et. al., J. Org. Chem., 27, 4054 (1962)] and the procedure illustrated below.

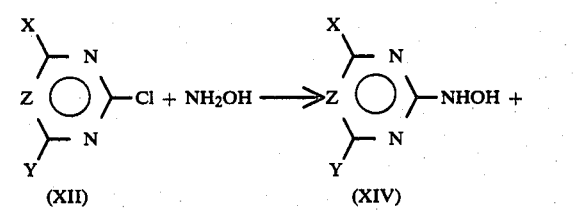

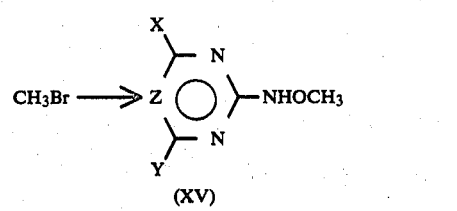

Chloro compound (XII) is reacted with hydroxylamine to form derivative (XIV) which may be alkylated with methyl bromide to afford the N-methoxy heterocyclic amine (XV). This compound may alternately be prepared in one step by treatment of (XII) and O-methyl hydroxylamine hydrochloride with an alkali metal hydroxide such as sodium hydroxide.

The compounds of this invention and their preparation are further illustrated by the following examples, wherein temperatures are given in degrees centigrade and parts are by weight unless otherwise indicated.

EXAMPLE 1

N-[(4,6-Dimethoxypyrimidin-2-yl)aminocarbonyl]sulfamic acid, (2-methylsulfonyloxy)phenyl ester To a cold (~10° C.) suspension of 0.6 g of 2-amino-4,6-dimethoxypyrimidine in 10 ml dry methylene chloride is added 1.5 g of 2-methylsulfonyloxyphenoxysulfonyl isocyanate. The reaction mixture exotherms mildly and is then stirred at room temperature for 18 hours. The resultant suspension is diluted with ethyl ether and the solid filtered to yield 1.1 g of white powder, m.p. 169°–171° C. The infrared spectrum shows absorption bands at 1730, 1620, 1570, 1350 cm$^{-1}$.

A mass spectral analysis shows a characteristic fragment pattern for the desired product.

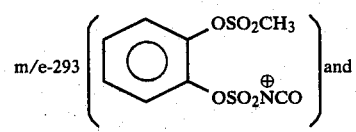

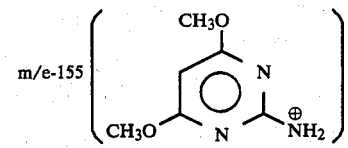

EXAMPLE 2

N-[(4-Methoxy-6-methyl-1,3,5-triazin-2-yl)aminocarbonyl]sulfamic acid, (2-methylsulfonyloxy)phenyl ester To 0.6 g of 2-amino-4-methoxy-6-methyl-1,3,5-triazine suspended in 10 ml acetonitrile is added 1.5 g of 2-methylsulfonyloxyphenoxysulfonyl isocyanate. The reaction mixture slowly exotherms (22° C.→28° C.) and a clear solution results. After stirring at room temperature ~1 hour, the solvent is evaporated under reduced pressure. The resultant crude oil is taken up in a minimum amount of chloroform and poured into ether to give a solid suspension. Filtration yields 1.0 g of white solid, m.p. 124°–126° C. The infrared spectrum shows absorption bands at 1720, 1610, 1550, 1350 cm$^{-1}$.

EXAMPLE 3

N-[(4,6-Dimethoxy-1,3,5-triazin-2-yl)-N-methylaminocarbonyl]sulfamic acid, (2-methylsulfonyloxy)phenyl ester To 0.7 g of 2-methylamino-4,6-dimethoxy-1,3,5-triazine suspended in 10 ml of acetonitrile is added 1.5 g of 2-methylsulfonyloxyphenoxysulfonyl isocyanate. The reaction mixture exotherms (23° C.→30° C.) and stirring is continued at room temperature ~1 hour. The solvent is evaporated under reduced pressure. The resultant crude oil is taken up in a minimum amount of chloroform and poured into ether to give a solid suspension. Filtration yields 1.2 g of white solid, m.p. 130°–133° C. The infrared spectrum shows absorption bands at 1715, 1560, 1360 cm⁻¹.

Using the procedures of Examples 1–3, the following compounds can be prepared. Tables I and II are meant to be illustrative of the breadth of this invention and are not meant to be all inclusive.

TABLE I

| R₁ | R₂ | R₃ | R₄ | Q | X | Y | Z | m.p. (°C.) |
|---|---|---|---|---|---|---|---|---|
| CH₃ | H | H | H | O | OCH₃ | OCH₃ | CH | 169–171° |
| CH₃ | H | H | H | O | OCH₃ | CH₃ | CH | 65–81° |
| CH₃ | H | H | H | O | CH₃ | CH₃ | CH | 68–95° |
| CH₃ | H | H | H | O | OCH₃ | OCH₃ | N | 134–139° |
| CH₃ | H | H | H | O | OCH₃ | CH₃ | N | 124–126° |
| CH₃ | H | H | H | O | CH₃ | CH₃ | N | 128–131° |
| CH₃ | H | H | H | O | OCH₂CH₂CH₃ | CH₃ | CH |  |
| CH₃ | H | H | H | O | CH₂OCH₃ | CH₃ | CH |  |
| CH₃ | H | H | H | O | CH₂CH₂CH₃ | OCH₃ | CH |  |
| CH₃ | H | H | H | O | OCH₂CF₃ | CH₃ | CH |  |
| CH₃ | H | H | H | O | CH₂CCl₃ | CH₃ | CH |  |
| CH₃ | H | H | H | O | CH₂CBr₃ | CH₃ | CH |  |
| CH₃ | H | H | H | O | CH₂CH₂Cl | CH₃ | CH |  |
| CH₃ | H | H | H | O | CH₂CH₂CH₂Cl | CH₃ | CH |  |
| CH₃ | H | H | H | O | CH₃ | H | CCH₃ |  |
| CH₃ | H | H | H | O | CH₃ | H | CCl |  |
| CH₃ | H | H | H | O | CH₂CF₃ | CH₃ | CH |  |
| 2,4-Cl₂-C₆H₃– | H | H | H | O | OCH₃ | OCH₃ | CH |  |
| 4-CF₃-C₆H₄– | H | H | H | O | OCH₃ | OCH₃ | CH |  |
| 2,4-(CH₃)₂-C₆H₃– | H | H | H | O | OCH₃ | OCH₃ | CH |  |
| 2-O₂N-C₆H₄– | H | H | H | O | OCH₃ | OCH₃ | CH |  |
| 2,4-(OCH₃)₂-C₆H₃– | H | H | H | O | OCH₃ | OCH₃ | CH |  |
| C₆H₅– | H | H | H | O | OCH₃ | OCH₃ | CH |  |
| CH₃ | H | H | H | –N–CH₃ | OCH₃ | OCH₃ | CH |  |
| CH₃ | H | H | H | –N–CH₂CH₂CH₂CH₃ | OCH₃ | OCH₃ | CH |  |
| CH₃ | H | H | H | O | CH₃ | H | CBr |  |
| CH₃ | H | H | H | O | CH₃ | H | CI |  |
| CH₃ | H | H | H | O | CH₃ | H | CF |  |
| –(CH₂)₃CH₃ | H | H | H | O | OCH₃ | OCH₃ | CH |  |
| –CH₂CH₂Cl | H | H | H | O | OCH₃ | OCH₃ | CH |  |
| –CH₃ | 4-F | 5-F | H | O | OCH₃ | OCH₃ | CH |  |
| –CH₃ | 4-Cl | 5-Cl | H | O | OCH₃ | OCH₃ | CH |  |
| –CH₃ | 4-Br | 5-Br | H | O | OCH₃ | OCH₃ | CH |  |
| –CH₃ | 4-OCH₃ | H | H | O | OCH₃ | OCH₃ | CH |  |
| –CH₃ | 6-NO₂ | H | H | O | OCH₃ | OCH₃ | CH |  |
| –CH₃ | 4-CH₃ | 5-CH₃ | H | O | OCH₃ | OCH₃ | CH |  |
| –CH₃ | H | H | CH₃ | O | OCH₃ | OCH₃ | N | 130–133° |

TABLE I-continued

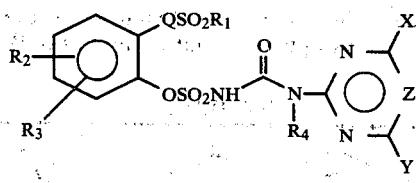

| R₁ | R₂ | R₃ | R₄ | Q | X | Y | Z | m.p. (°C.) |
|---|---|---|---|---|---|---|---|---|
| CF₃ | H | H | H | O | OCH₃ | OCH₃ | CH | |
| CF₃ | H | H | H | O | OCH₃ | CH₃ | CH | |
| CF₃ | H | H | H | O | CH₃ | CH₃ | CH | |
| CF₃ | H | H | H | O | OCH₃ | OCH₃ | N | |
| CF₃ | H | H | H | O | OCH₃ | CH₃ | N | |
| CF₃ | H | H | H | O | CH₃ | CH₃ | N | |
| CF₃ | H | H | H | N—CH₃ | OCH₃ | OCH₃ | CH | |
| CF₃ | H | H | H | N—CH₃ | OCH₃ | CH₃ | CH | |
| CF₃ | H | H | H | N—CH₃ | CH₃ | CH₃ | CH | |
| CF₃ | H | H | H | N—CH₃ | OCH₃ | OCH₃ | N | |
| CF₃ | H | H | H | N—CH₃ | OCH₃ | CH₃ | N | |
| CF₃ | H | H | H | N—CH₃ | CH₃ | CH₃ | N | |
| CH₃ | H | H | H | N—CH₃ | OCH₃ | CH₃ | CH | |
| CH₃ | H | H | H | N—CH₃ | CH₃ | CH₃ | CH | |
| CH₃ | H | H | H | N—CH₃ | OCH₃ | OCH₃ | N | |
| CH₃ | H | H | H | N—CH₃ | OCH₃ | CH₃ | N | |
| CH₃ | H | H | H | N—CH₃ | CH₃ | CH₃ | N | |
| CH₂(CH₂)₂Cl | H | H | H | O | OCH₃ | OCH₃ | CH | |
| CH₂(CH₂)₃Cl | H | H | H | O | OCH₃ | OCH₃ | CH | |
| CH₂CH₂OCH₃ | H | H | H | O | OCH₃ | OCH₃ | CH | |
| CH₂CH₂CH₂OCH₃ | H | H | H | O | OCH₃ | OCH₃ | CH | |
| 2-F-C₆H₄ | H | H | H | O | OCH₃ | OCH₃ | CH | |
| 4-Br-C₆H₄ | H | H | H | O | OCH₃ | OCH₃ | CH | |
| 2-Cl-C₆H₄ | H | H | H | O | OCH₃ | OCH₃ | CH | |
| 2,6-Cl₂-C₆H₃ | H | H | H | O | OCH₃ | OCH₃ | CH | |
| CH₃ | H | H | H | O | NH₂ | Cl | CH | |
| CH₃ | H | H | H | O | NHCH₃ | Cl | CH | |
| CH₃ | H | H | H | O | N(CH₃)₂ | Cl | CH | |
| CH₃ | H | H | H | O | OCH₃ | Cl | CH | |
| CH₃ | H | H | H | O | CH₃ | Cl | CH | |
| CH₃ | H | H | H | O | OCH₃ | H | CH | |
| CH₃ | H | H | H | O | CH₃ | H | CH | |
| CH₃ | H | H | H | O | CH₂OCH₃ | H | CH | |
| CH₃ | H | H | H | O | CH₂(CH₂)₂CH₃ | CH₃ | CH | |
| CH₃ | H | H | H | O | CH₂OCH₂CH₃ | CH₃ | CH | |
| CH₃ | H | H | H | O | —OCH₂CH=CH₂ | CH₃ | CH | 84–88° |
| CH₃ | H | H | H | O | —OCH₂CH=CH₂ | OCH₃ | N | |
| CH₃ | H | H | H | O | —OCH₂CH=CHCH₃ | CH₃ | CH | |
| CH₃ | H | H | H | O | —OCH₂C(CH₃)=CH₂ | CH₃ | CH | |
| CH₃ | H | H | H | O | —OCH₂C≡CH | CH₃ | CH | |
| CH₃ | H | H | H | O | —OCH₂C≡CCH₃ | CH₃ | CH | |
| CH₃ | H | H | H | O | —OCH₂CH₂C≡CH | CH₃ | CH | |
| CH₃ | 4-CH₂CH₃ | H | H | O | CH₃ | OCH₃ | CH | |
| CH₃ | H | H | CH₃ | O | OCH₃ | OCH₃ | CH | |
| CH₃ | H | H | OCH₃ | O | OCH₃ | OCH₃ | CH | |
| CH₂Cl | H | H | H | O | OCH₃ | OCH₃ | CH | 116–119° |
| CH₂Cl | H | H | H | O | OCH₃ | CH₃ | CH | 93–95° |
| CH₂Cl | H | H | H | O | CH₃ | CH₃ | CH | 154–158° |
| CH₂Cl | H | H | H | O | OCH₃ | OCH₃ | N | 154–158° |

TABLE I-continued

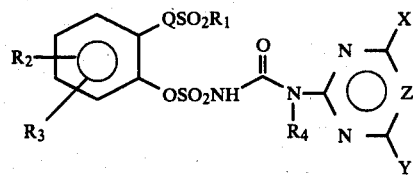

| R₁ | R₂ | R₃ | R₄ | Q | X | Y | Z | m.p. (°C.) |
|---|---|---|---|---|---|---|---|---|
| —C₆H₅ (phenyl) | H | H | H | O | OCH₃ | CH₃ | CH | 90–95° |

TABLE II

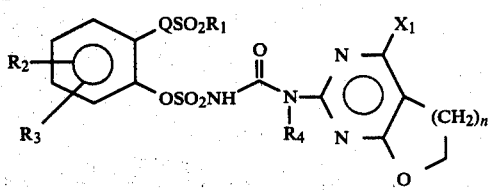

| R₁ | R₂ | R₃ | R₄ | Q | X₁ | n | m.p. (°C.) |
|---|---|---|---|---|---|---|---|
| CH₃ | H | H | H | O | H | 1 | |
| CH₃ | H | H | H | O | CH₃ | 1 | |
| CH₃ | H | H | H | O | OCH₃ | 1 | |
| —C₆H₄—Cl | H | H | H | O | CH₃ | 1 | |
| —CH₂CH₂Cl | H | H | H | O | CH₃ | 2 | |
| CH₃ | H | H | H | —N—CH₃ | CH₃ | 2 | |
| CH₃ | H | H | H | —N—(CH₂)₃CH₃ | CH₃ | 2 | |
| —(CH₂)₃CH₃ | H | H | H | O | CH₃ | 1 | |
| —CH₂CF₃ | H | H | H | O | CH₃ | 1 | |
| —CH₂CCl₃ | H | H | H | O | CH₃ | 1 | |
| —CH₂CBr₃ | H | H | H | O | CH₃ | 1 | |
| —C₆H₄—OCH₃ | H | H | H | O | CH₃ | 2 | |
| —C₆H₄—NO₂ | H | H | H | O | CH₃ | 2 | |
| —C₆H₄—CH₃ | H | H | H | O | CH₃ | 1 | |
| —C₆H₅ | H | H | H | O | CH₃ | 1 | |
| CH₃ | H | H | CH₃ | O | CH₃ | 1 | |
| —C₆H₄—CF₃ | H | H | H | O | CH₃ | 2 | |
| —C₆H₄—F | H | H | H | O | CH₃ | 1 | |
| —C₆H₄—Br | H | H | H | O | CH₃ | 2 | |

TABLE II-continued

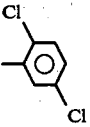

| $R_1$ | $R_2$ | $R_3$ | $R_4$ | Q | $X_1$ | n | m.p. (°C.) |
|---|---|---|---|---|---|---|---|
| Cl-⟨⟩-⟨⟩-Cl | H | H | H | O | $CH_3$ | 1 | |
| $CH_3$ | H | H | H | O | Cl | 1 | |
| $CH_3$ | H | H | H | O | Cl | 2 | |
| $CF_3$ | H | H | H | O | $CH_3$ | 1 | |
| $CH_3$ | H | H | $CH_3$ | O | $CH_3$ | 2 | |

TABLE III

| $R_1$ | $R_2$ | $R_3$ | $R_4$ | Q | $X_1$ | m.p. (°C.) |
|---|---|---|---|---|---|---|
| $CH_3$ | H | H | H | O | H | |
| $CH_3$ | H | H | H | O | $CH_3$ | |
| $CH_3$ | H | H | H | O | $OCH_3$ | |
| $CH_3$ | H | H | H | O | Cl | |
| $-CH_2Cl$ | H | H | H | O | $CH_3$ | |
| $CH_3$ | H | H | H | $N-CH_3$ | $CH_3$ | |
| $CF_3$ | H | H | H | O | $OCH_3$ | |
| $CH_3$ | H | H | $CH_3$ | O | $CH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically they will contain these ingredients in the following approximate proportions:

TABLE IV

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, March 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

| Wettable Powder | |
|---|---|
| N—[(4,6-dimethoxypyrimidin-2-yl)aminocarbonyl]-sulfamic acid, [2-(methylsulfonyloxy)phenyl] ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 5

| Wettable Powder | |
|---|---|
| N—[(4-methoxy-6-methylpyrimidin-2-yl)aminocarbonyl]-sulfamic acid, [2-(methylsulfonyloxy)phenyl] ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 6

| Granule | |
|---|---|
| wettable powder of Example 5 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 7

| Extruded Pellet | |
|---|---|
| N—[(4,6-dimethylpyrimidin-2-yl)aminocarbonyl-sulfamic acid, [2-(methylsulfonyloxy)phenyl] ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

| Oil Suspension | |
|---|---|
| N—[(4,6-dimethoxy-1,3,5-triazin-2-yl)aminocarbonyl]-sulfamic acid, [2-(methylsulfonyloxy)phenyl] ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

| Wettable Powder | |
|---|---|
| N—[(4,6-dimethyl-1,3,5-triazin-2-yl)aminocarbonyl]-sulfamic acid, [2-(methylsulfonyloxy)phenyl] ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

| Low Strength Granule | |
|---|---|
| N—[(4-methoxy-6-methyl-1,3,5-triazin-2-yl)aminocarbonyl]-sulfamic acid, [2-(methylsulfonyloxy)phenyl] ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

| Aqueous Suspension | |
|---|---|
| N—[(4,6-dimethoxypyrimidin-2-yl)aminocarbonyl]- | |

-continued

Aqueous Suspension

| | |
|---|---|
| sulfamic acid, [2-(methylsulfonyloxy)phenyl] ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 12

Solution

| | |
|---|---|
| N—[(4-methoxy-6-methylpyrimidin-2-yl)aminocarbonyl]-sulfamic acid, [2-(methylsulfonyloxy)phenyl] ester, sodium salt | 5% |
| water | 95% |

The salt is added directly to the water with stirring to produce the solution, which may then be packaged for use.

EXAMPLE 13

Low Strength Granule

| | |
|---|---|
| N—[(4,6-dimethylpyrimidin-2-yl)aminocarbonyl-sulfamic acid, [2-(methylsulfonyloxy)phenyl] ester | 0.1% |
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 14

Granule

| | |
|---|---|
| N—[(4,6-dimethoxy-1,3,5-triazin-2-yl)aminocarbonyl]-sulfamic acid, [2-(methylsulfonyloxy)phenyl] ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 15

High Strength Concentrate

| | |
|---|---|
| N—[(4,6-dimethyl-1,3,5-triazin-2-yl)aminocarbonyl]-sulfamic acid, [2-(methylsulfonyloxy)phenyl] ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

Wettable Powder

| | |
|---|---|
| N—[(4,6-dimethoxypyrimidin-2-yl)aminocarbonyl]-sulfamic acid, [2-(methylsulfonyloxy)phenyl] ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 17

Wettable Powder

| | |
|---|---|
| N—[(4,6-dimethoxypyrimidin-2-yl)aminocarbonyl-sulfamic acid, [2-(methylsulfonyloxy)phenyl] ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| N—[(4-methoxy-6-methylpyrimidin-2-yl)aminocarbonyl]-sulfamic acid, [2-(methylsulfonyloxy)phenyl] ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| N—[(4,6-dimethoxypyrimidin-2-yl)aminocarbonyl]sulfamic acid, [2-(methylsulfonyloxy)phenyl] ester | 10% |
| attapulgite | 10% |
| pyrophyllite | 80% |

The active ingredient is blended with attapulgite and then passed through a hammer mill to produce particles substantially all below 200 microns. The ground concentrate is then blended with powdered pyrophyllite until homogeneous.

Utility

The compounds of the present invention are active herbicides. They have utility for broadspectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application, compounds of this invention may be used to modify plant growth beneficially, and also selectively control weeds in crops such as rice and wheat.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention can be used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H, 3H)-dione (hexazinone); N,N-dimethyl-2,2-diphenylacetamide (diphenamide); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)-phenoxy]propanoate (diclofop methyl); 4-amino-6-tertbutyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl(methoxymethyl)acetanilide (alachlor); 1,1-dimethyl-3-(α,α,α-trifluoro-m-tolyl)urea (fluometuron); 5-[2-chloro-4-(trifluoromethyl)phenoxy]-2-nitrobenzoic acid, methyl ester (acifluorfen-methyl); S-[(4-chlorophenyl)methyl]diethylcarbamothioate (thiobencarb); N-(butoxymethyl)-2-chloro-2',6'-diethylacetanilide (butachlor); 2,4-dichlorophenyl p-nitrophenyl ether (nitrofen); S-ethyl hexahydro-1-azepine-1-carbothioate (molinate); 2-tert-butyl-4-(2,4-dichloro-5-isopropoxyphenyl)-Δ²-1,3,4-oxadiazolin-5-one (oxadiazon); 2,4-dichlorophenyl-3-methoxy-4-nitrophenyl ether; 1-(α,α-dimethylbenzyl)-3-(4-methylphenyl)urea; 2-methylthio-4,6-bis(ethylamino)-s-triazine; 4-(2,4-dichlorobenzoyl)-1,3-dimethylpyrazol-5-yl-p-toluenesulfonate; α-(β-naphthyloxy)propionanilide; and 2-chloro-2',6'-diethyl-N-(N-propoxyethyl)acetanilide.

The activity of these compounds was discovered in greenhouse tests. The tests are described and the data resulting from them are shown below.

TEST PROCEDURE A

Seeds of crabgrass (*Digitaria spp.*), barnyardgrass (*Echinochloa crusgalli*), wild oats (*Avena fatua*), cassia (*Cassia tora*), morningglory (Ipomoea spp.), cocklebur (*Xanthium spp.*), sorghum, corn, soybean, rice, wheat and nutsedge tubers (*Cyperus rotundus*) were planted in a growth medium and treated pre-emergence with a nonphytotoxic solvent solution of the compounds of Table IV. At the same time, cotton having five leaves (including cotyledonary ones), bush beans with the third trifoliolate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledondary leaves, rice with three leaves, wheat with one leaf, and nutsedge with threefive leaves were sprayed with a nonphytotoxic solvent solution of the compounds of Table V. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0 = no effect;
10 = maximum effect;
C = chlorosis or necrosis;
D = defoliation;
E = emergence inhibition;
G = growth retardation;
H = formative effects;
U = unusual pigmentation;
X = axillary stimulation; and
6Y = abscised buds or flowers.

It can be seen from Table V that several compounds from within the scope of the invention have utility for selective pre- and/or post-emergence weed control in wheat.

Compound 1

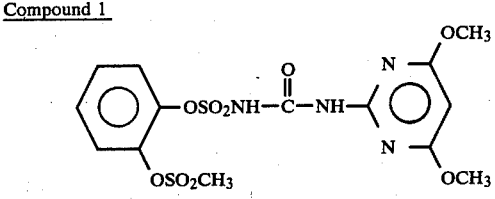

Compound 2

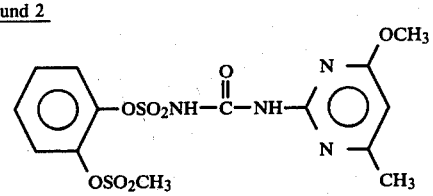

Compound 3
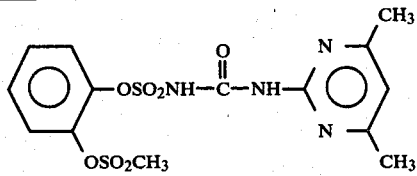

Compound 4
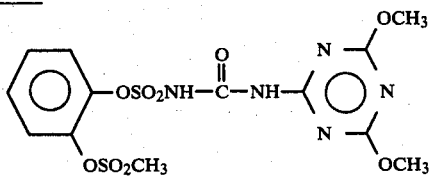

Compound 5
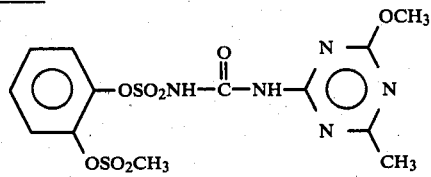

Compound 6
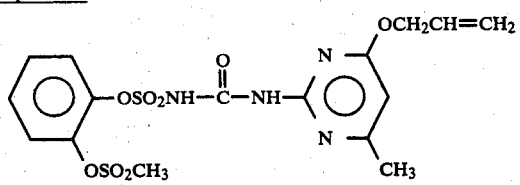

Compound 7
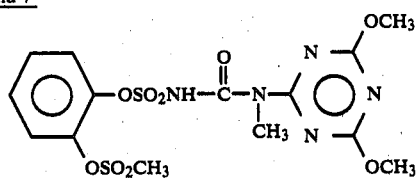

Compound 8
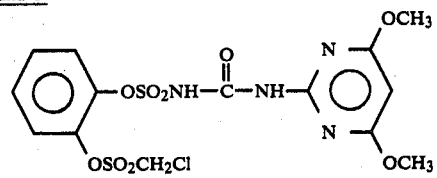

Compound 9
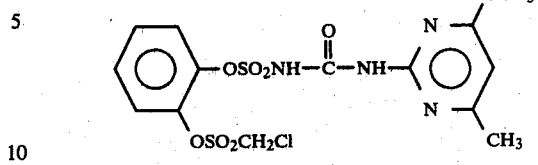

Compound 10
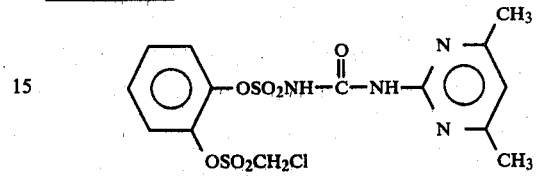

Compound 11
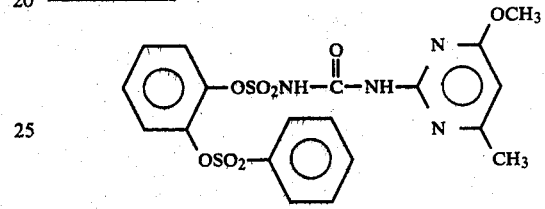

Compound 12
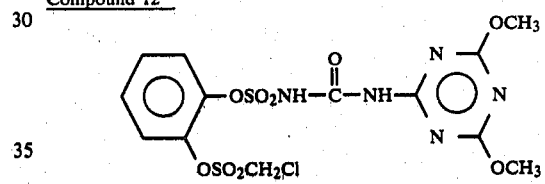

Compound 13
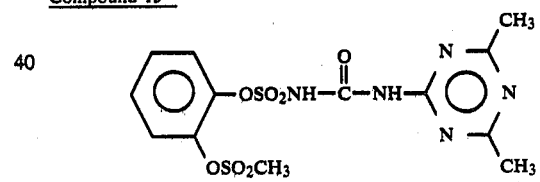

TABLE V

| | Compound Nos. | | | | | | |
|---|---|---|---|---|---|---|---|
| | 1 | 2 | 3 | 4 | 5 | 6 | 7 |
| Rate kg/ha | 0.4 | 0.4 | 0.4 | 0.4 | 0.4 | 0.4 | 0.4 |
| POST-EMERGENCE | | | | | | | |
| Bush Bean | 9C | 9C | 6C,9G,6Y | 2C,5G | 1C,1H | 1C | 7 |
| Cotton | 9C,9G | 2U,5C,9G | 7C,9G | 2C | 1C | 1C | 2B |
| Morningglory | 10C | 10C | 4C,9G | 0 | 1C | 2C,7H | 9C |
| Cocklebur | 10C | 10C | 10C | 1C | 1C,5H | 1C,4G | 9C |
| Cassia | 9C | 3C,5G | 3C | 1C | 1C | 1C | 0 |
| Nutsedge | 9C | 2C,7G | 2C | 0 | 0 | 0 | 0 |
| Crabgrass | 2C,5G | 3C,6G | 0 | 0 | 0 | 0 | 0 |
| Barnyardgrass | 5C,9H | 2C,8H | 0 | 1C | 1H | 0 | 0 |
| Wild Oats | 1C,3G | 2C | 0 | 0 | 0 | 0 | 0 |
| Wheat | 1C,3G | 0 | 0 | 0 | 0 | 0 | 0 |
| Corn | 4C,8H | 3C,8H | 1C,6H | 2C,9H | 7H | 0 | 0 |
| Soybean | 10C | 3C,9G | 3C,7G,5X | 2C,2H | 1C,3G | 1C,5G | 6G |
| Rice | 1C,4G | 1C,3G | 1C | 2C,7G | 3G | 0 | 0 |

TABLE V-continued

| | | | | | | | |
|---|---|---|---|---|---|---|---|
| Sorghum | 5C,9H | 4C,9H | 2C,9G | 2C,9G | 3C,9H | 2C | 6G |

| | Compound Nos. | | | | | |
|---|---|---|---|---|---|---|
| | 8 | 9 | 10 | 11 | 12 | 13 |
| Rate kg/ha | 0.4 | 0.4 | 0.4 | 0.4 | 0.4 | 2.0 |
| Bush Bean | 7C,7G,6Y | 2C,3G | 2C,2G | 0 | 0 | 2C,5G,6Y |
| Cotton | 7C,4G | 7C,5G | 5C,3G | 0 | 1C | 1C,2G |
| Morningglory | 10C | 10C | 3C,3G | 1C,4G | 2C,8H | 1C,6G |
| Cocklebur | 7C,5G | 3C,5G | 5C,6G | 1C | 1C | 1C,6G |
| Cassia | 5C,6G | 2C,3G | 2C,3G | 1C | 2C,3G | 2C |
| Nutsedge | 3C,5G | 0 | 0 | 0 | 0 | 0 |
| Crabgrass | 2G,2C | 0 | 0 | 0 | 0 | 0 |
| Barnyardgrass | 0 | 2C,3G | 0 | 0 | 0 | 2H |
| Wild Oats | 0 | 0 | 0 | 0 | 0 | 0 |
| Wheat | 0 | 0 | 0 | 0 | 0 | 0 |
| Corn | 0 | 6C,4G | 0 | 0 | 3G | 2C |
| Soybean | 7C,6G | 7C,6G | 4C,3G | 1H | 1C,1H | 2H,6G |
| Rice | 0 | 0 | 0 | 0 | 1C | 3G |
| Sorghum | 0 | 2C,3G | 2C,4G | 0 | 3C,9H | 7H |

| | Compound Nos. | | | | | |
|---|---|---|---|---|---|---|
| | 1 | 2 | 3 | 4 | 5 | 6 | 7 |
| Rate kg/ha | 0.4 | 0.4 | 0.4 | 0.4 | 0.4 | 0.4 | 0.4 |
| | PRE-EMERGENCE | | | | | | |
| Morningglory | 9G | 2C,9G | 3C,9G | 9G | 0 | 3C | 2C,9G |
| Cocklebur | 9H | 9H | 9G | 9H | 9H | 9H | 9C |
| Cassia | 3C,9G | 6C,9G | 8C | 2G | 2C | 0 | 1C |
| Nutsedge | 10E | 10E | 1C,8G | 0 | 1C,5G | 0 | 0 |
| Crabgrass | 3C,6G | 2C,6G | 1C | 2C | 2C | 0 | 0 |
| Barnyardgrass | 2C,9H | 3C,9H | 2C,9G | 2C,8H | 2C,7H | 2C | 1C |
| Wild Oats | 1C,4G | 3C,8G | 1C,5G | 2C,3G | 3C | 0 | 0 |
| Wheat | 1C,3G | 1C,7G | 2G | 8G | 8G | 0 | 0 |
| Corn | 2C,9G | 3U,9G | 1U,9H | 2C,8G | 2C,9G | 2C,5G | 1C,5G |
| Soybean | 9H | 9H | 2C,9H | 2C | 2C | 0 | 1C |
| Rice | 2C,7G | 2C,9H | 3C,9H | 2C,9H | 2C,7G | 0 | 2C |
| Sorghum | 5C,9H | 10H | 10H | 5C,9G | 1C,9H | 2C,6G | 3G |

| | Compound Nos. | | | | | |
|---|---|---|---|---|---|---|
| | 8 | 9 | 10 | 11 | 12 | 13 |
| Rate kg/ha | 0.4 | 0.4 | 0.4 | 0.4 | 0.4 | 2.0 |
| Morningglory | 3C,5G | 10C | 5C,4G | 4G | 9G | 0 |
| Cocklebur | 2C,5G | 3C,5G | 4C,3G | 9H | 8H | 0 |
| Cassia | 7C,8G | 5C,5G | 6C,8G | 2C | 2C,3G | 0 |
| Nutsedge | 10E | 10E | 0 | 0 | 2G | 0 |
| Crabgrass | 2C,3G | 3C,4G | 3G | 1C | 0 | 0 |
| Barnyardgrass | 6C,5G | 7C,6G | 0 | 0 | 2C | 0 |
| Wild Oats | 0 | 0 | 0 | 0 | 2C,3G | 0 |
| Wheat | 0 | 0 | 0 | 0 | 0 | 0 |
| Corn | 2C,4G | 4C,5G | 2C,4G | 0 | 2C,8G | 0 |
| Soybean | 7C,6G | 7C,6G | 5C,4G | 1H | 1C | 0 |
| Rice | 2G | 3C,4G | 0 | 1C,3G | 2C | 0 |
| Sorghum | 3C,6G | 7C,7G | 5C,7G | 0 | 1C,9H | 0 |

TEST PROCEDURE B

The following examples demonstrate the excellent utility some of the compounds of the present invention have as selective herbicides for the control of weeds in rice cultures. The results presented in Tables VI and VII show them to be active against various weeds (barnyardgrass, water chestnut, arrowhead, Scirpus) yet to cause little or no injury to rice plants:

EXAMPLE I

Three days after transplanting of rice into paddies, the compounds to be tested were formulated and applied directly to the paddy water. The paddies were maintained in a greenhouse, and plant response ratings were taken at approximately one and four weeks after application, as illustrated in Table VI.

TABLE VI

| Cpd. No. | Application Rate, Grams Per Hectare | Rice 1 week | Rice 4 weeks | Barn-yard Grass* 4 weeks | Water Chestnut* 4 weeks | Arrow-head* 4 weeks |
|---|---|---|---|---|---|---|
| 1 | 100 | 0 | 1G | 9C | 10C | 10E |
| | 400 | 0 | 2G | 10C | 10C | 10E |
| 2 | 100 | 0 | 1G | 6G | 10G,3C | 10E |
| | 400 | 0 | 3G | 9C | 10C | 10E |
| 3 | 100 | 0 | 2G | 0 | 0 | 0 |
| | 400 | 0 | 4G | 8C | 10C | 4C,4H |

*Echinochloa sp., Eleocharis sp., and Sagittaria sp., respectively.

EXAMPLE II

Three days after transplanting of rice into paddies, the compounds to be tested were formulated and applied directly to the paddy water. The paddies were maintained in a greenhouse, and plant response ratings were taken four and thirty-two days after application as illustrated in Table VII.

TABLE VII

| Cpd. No. | Application Rate, Grams Per Hectare | Rice 4 Days | Rice 32 Days | Barnyard-Grass* 32 Days | Water Chestnut* 32 Days | Arrowhead* 32 Days | Scirpus* 32 Days |
|---|---|---|---|---|---|---|---|
| 1 | 10 | 0 | 0 | 2G | 9G | 1G | 5G |
|  | 15 | 0 | 0 | 4G | 10C | 2G | 10C |
|  | 20 | 0 | 0 | 4G | 10C | 3G | 10C |
|  | 25 | 0 | 0 | 5G | 10C | 8G | 10C |
| 8 | 25 | 0 | 0 | 0 | 0 | 0 | 1G |
|  | 75 | 0 | 0 | 1G | 10C | 0 | 10C |
| 9 | 25 | 0 | 0 | 0 | 9G | 1G,2C | 0 |
|  | 75 | 0 | 0 | 1G | 10C | 3G,4C | 10C |

*Echinochloa sp., Eleocharis sp., Sagittaria sp., and Scirpus sp., respectively.

What is claimed is:

1. A compound of the formula:

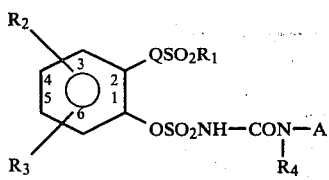

where
Q is O or $NR_5$;
$R_1$ is $C_1$-$C_4$ alkyl, $C_1$-$C_4$ alkyl substituted with 1-3 atoms of F, Cl or Br, $CH_2CH_2OCH_3$, $CH_2CH_2CH_2OCH_3$ or

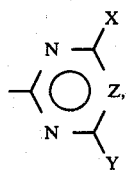

$R_2$ is H, F, Cl, Br, $OCH_3$, $NO_2$ or $C_1$-$C_2$ alkyl;
$R_3$ is H, F, Cl, Br or $CH_3$;
$R_4$ is H, $CH_3$ or $OCH_3$;
$R_5$ is $C_1$-$C_4$ alkyl;
$R_6$ and $R_7$ are independently H, F, Cl, Br, $CH_3$, $CF_3$, $NO_2$ or $OCH_3$;
A is

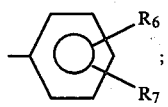

X is $NH_2$, $N(CH_3)_2$, $NHCH_3$, $C_1$-$C_4$ alkyl, $CH_2OCH_3$, $CH_2OC_2H_5$, $C_1$-$C_3$ alkoxy, $C_3$-$C_4$ alkenyloxy, $C_3$-$C_4$ alkynyloxy, $OCH_2CF_3$ or $C_1$-$C_3$ alkyl substituted with 1-3 atoms of F, Cl or Br;
Y is H, $CH_3$, $OCH_3$ or Cl;
Z is CH, $CCH_3$, CBr, CCl, CF or CI
provided that:
(1) when Y is Cl, then Z is CH and X is $NH_2$, $NHCH_3$, $N(CH_3)_2$, $CH_3$ or $OCH_3$; and
(2) when Y is H, then X is $OCH_3$, $CH_3$ or $CH_2OCH_3$, and Z is CH, $CCH_3$, CBr, CCl, CF or CI.

2. A compound of claim 1 where $R_5$ is $CH_3$ and $R_4$ is H or $CH_3$.

3. A compound of claim 2 where $R_1$ is $C_1$-$C_4$ alkyl or $CF_3$.

4. A compound of claim 3 where $R_2$ is H.

5. A compound of claim 4 where $R_3$ is H.

6. A compound of claim 5 where
$R_1$ is $C_1$-$C_3$ alkyl or $CF_3$;
Q is O;
A is

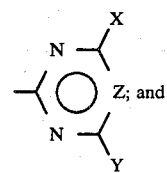

Z is CH.

7. A compound of claim 6 where $R_4$ is H.

8. A compound of claim 7 where X and Y are independently $CH_3$ or $OCH_3$, and $R_1$ is $CH_3$.

9. The compound of claim 1, N-[(4,6-dimethoxypyrimidin-2-yl)aminocarbonyl]sulfamic acid, [2-(methylsulfonyloxy)phenyl]ester.

10. The compound of claim 1, N-[(4-methoxy-6-methylpyrimidin-2-yl)aminocarbonyl]sulfamic acid, [2-(methylsulfonyloxy)phenyl]ester.

11. The compound of claim 1, N-[(4,6-dimethylpyrimidin-2-yl)aminocarbonyl]sulfamic acid, [2-(methylsulfonyloxy)phenyl]ester.

12. A composition suitable for controlling the growth of undesired vegetation which comprises an effective amount of a compound of claim 1 and at least one of the following: surfactant, solid or liquid inert diluent.

13. A composition suitable for controlling the growth of undesired vegetation which comprises an effective amount of a compound of claim 2 and at least one of the following: surfactant, solid or liquid inert diluent.

14. A composition suitable for controlling the growth of undesired vegetation which comprises an effective amount of a compound of claim 3 and at least one of the following: surfactant, solid or liquid inert diluent.

15. A composition suitable for controlling the growth of undesired vegetation which comprises an effective amount of a compound of claim 4 and at least one of the following: surfactant, solid or liquid inert diluent.

16. A composition suitable for controlling the growth of undesired vegetation which comprises an effective amount of a compound of claim 5 and at least one of the following: surfactant, solid or liquid inert diluent.

17. A composition suitable for controlling the growth of undesired vegetation which comprises an effective amount of a compound of claim 6 and at least one of the following: surfactant, solid or liquid inert diluent.

18. A composition suitable for controlling the growth of undesired vegetation which comprises an effective amount of a compound of claim 7 and at least one of the following: surfactant, solid or liquid inert diluent.

19. A composition suitable for controlling the growth of undesired vegetation which comprises an effective amount of the compound of claim 8 and at least one of the following: surfactant, solid or liquid inert diluent.

20. A method for controlling the growth of undesired vegetation which comprises applying to the locus to be protected an effective amount of a compound of claim 1.

21. A method for controlling the growth of undesired vegetation which comprises applying to the locus to be protected an effective amount of a compound of claim 2.

22. A method for controlling the growth of undesired vegetation which comprises applying to the locus to be protected an effective amount of a compound of claim 3.

23. A method for controlling the growth of undesired vegetation which comprises applying to the locus to be protected an effective amount of a compound of claim 4.

24. A method for controlling the growth of undesired vegetation which comprises applying to the locus to be protected an effective amount of a compound of claim 5.

25. A method for controlling the growth of undesired vegetation which comprises applying to the locus to be protected an effective amount of a compound of claim 6.

26. A method for controlling the growth of undesired vegetation which comprises applying to the locus to be protected an effective amount of a compound of claim 7.

27. A method for controlling the growth of undesired vegetation which comprises applying to the locus to be protected an effective amount of the compound of claim 8.

28. A method for controlling the growth of undesired vegetation in rice without damage to the rice which comprises applying to the locus to be protected an effective amount of N-[(4,6-dimethoxy-pyrimidin-2-yl)aminocarbonyl]sulfamic acid, [2-(methylsulfonyloxy)-phenyl]ester.

* * * * *